(12) United States Patent
Truong

(10) Patent No.: US 11,185,845 B1
(45) Date of Patent: Nov. 30, 2021

(54) WATER EXTRACTABLE MICROCAPSULES OF ACTIVATED CARBON, SUPER ACTIVATED CARBON, AND OTHER ADSORPTIVE AND REACTIVE MATERIALS

(71) Applicant: U.S. Government as Represented by the Secretary of the Army, Natick, MA (US)

(72) Inventor: Quoc Truong, Hyde Park, MA (US)

(73) Assignee: U.S. Government as Represented by the Secretary of the Army, Washington, DC (US)

( * ) Notice: Subject to any disclaimer, the term of this patent is extended or adjusted under 35 U.S.C. 154(b) by 787 days.

(21) Appl. No.: 15/834,283

(22) Filed: Dec. 7, 2017

(51) Int. Cl.
| | |
|---|---|
| *A61L 9/014* | (2006.01) |
| *B01J 20/20* | (2006.01) |
| *B01J 20/28* | (2006.01) |
| *B01J 20/26* | (2006.01) |
| *B01J 20/30* | (2006.01) |
| *B01J 20/32* | (2006.01) |
| *B01D 71/02* | (2006.01) |
| *B01D 69/14* | (2006.01) |
| *B01D 53/22* | (2006.01) |
| *B01J 20/22* | (2006.01) |

(52) U.S. Cl.
CPC ......... *B01J 20/28033* (2013.01); *A61L 9/014* (2013.01); *B01D 53/228* (2013.01); *B01D 69/147* (2013.01); *B01D 69/148* (2013.01); *B01D 71/021* (2013.01); *B01J 20/20* (2013.01); *B01J 20/226* (2013.01); *B01J 20/261* (2013.01); *B01J 20/28021* (2013.01); *B01J 20/3042* (2013.01); *B01J 20/3225* (2013.01); *B01J 20/3295* (2013.01); *A61L 2209/14* (2013.01); *A61L 2209/22* (2013.01)

(58) Field of Classification Search
CPC ... B01D 53/228; B01J 20/28033; B01J 20/20; B01J 20/261; B01J 20/28021; B01J 20/3293; A61L 9/04
See application file for complete search history.

(56) References Cited

U.S. PATENT DOCUMENTS

| | | | |
|---|---|---|---|
| 6,458,458 | B1 | 10/2002 | Cooke et al. |
| 6,479,571 | B1 | 11/2002 | Cooke et al. |
| 2002/0110689 | A1* | 8/2002 | Hu ............................ B01J 20/20 428/375 |
| 2002/0197396 | A1 | 12/2002 | Haggquist |
| 2003/0082382 | A1 | 5/2003 | Hiltzik et al. |
| 2004/0018359 | A1 | 1/2004 | Haggquist |
| 2006/0251609 | A1 | 11/2006 | Sojka et al. |
| 2007/0173154 | A1 | 7/2007 | Hartmann et al. |
| 2011/0113538 | A1 | 5/2011 | von Blucher et al. |
| 2015/0240415 | A1 | 8/2015 | Haggquist |

FOREIGN PATENT DOCUMENTS

| | | | |
|---|---|---|---|
| JP | S60238139 A | 11/1985 | |
| WO | WO-2017018569 A1 * | 2/2017 | ........... C25B 11/043 |

OTHER PUBLICATIONS

Kubacka et al., Scientific Reports, (2014), p. 1-9.*

* cited by examiner

*Primary Examiner* — Yong L Chu
(74) *Attorney, Agent, or Firm* — Roger C. Phillips

(57) ABSTRACT

The disclosed subject matter relates to a microcapsule including a particle core selected from activated carbon (AC), super activated carbon (SAC), MOF composition, multifunctional material or a mixture thereof and a water-soluble polymer shell, including a membrane into which the microcapsule is incorporated, a membrane with exposed AC, SAC, MOF, or multifunctional materials or mixture thereof formed therefrom and methods used is the formation of all of the above.

3 Claims, 4 Drawing Sheets

| Formulation | PVOH (g) | Water (mL) | AC (g) |
|---|---|---|---|
| 1 | 17.5 | 175 | 17.5 |
| 2 | 25 | 250 | 10 |
| 3 | 25 | 175 | 17.5 |
| 4 | 17.5 | 250 | 17.5 |
| 5 | 10 | 175 | 17.5 |
| 6 | 17.5 | 175 | 25 |
| 7 | 10 | 250 | 10 |
| 8 | 25 | 250 | 25 |
| 9 | 25 | 100 | 25 |
| 10 | 10 | 100 | 10 |
| 11 | 17.5 | 100 | 17.5 |
| 12 | 10 | 250 | 25 |
| 13 | 25 | 100 | 10 |
| 14 | 17.5 | 175 | 17.5 |
| 15 | 17.5 | 175 | 10 |
| 16 | 10 | 100 | 25 |

FIG. 3

| Formulation | Capsule Yield (g) | Clustering | Uniformity (size) | Uniformity (shape) | Surface Area (m²/g) |
|---|---|---|---|---|---|
| 1 | 0.590 | 2 | 1 | 1 | 133.5 |
| 2 | 0.635 | 1 | 2 | 1 | 48.36 |
| 3 | 0.306 | 2 | 2-3 | 1 | 48.87 |
| 4 | 2.056 | 1 | 1 | 1 | 85.23 |
| 5 | 2.667 | 1 | 1 | 2 | 241.4 |
| 6 | 1.033 | 2-3 | 1 | 1-2 | 129.4 |
| 7 | 1.919 | 2 | 1 | 2 | 230.0 |
| 8 | 2.115 | 2-3 | 2 | 2 | 76.66 |
| 9 | 0.015 | 1 | 2 | 2-3 | - |
| 10 | 0.081 | 2 | 1 | 1 | - |
| 11 | 0.209 | 1 | 2 | 1 | 175.0 |
| 12 | 3.872 | 2 | 2 | 1 | 519.7 |
| 13 | 0.0082 | 2 | 1 | 2 | - |
| 14 | 1.078 | 2-3 | 2 | 1 | 103.5 |
| 15 | 0.965 | 2 | 2 | 1 | - |
| 16 | 2.345 | 2 | 2 | 1 | 354.7 |

FIG. 5

WATER EXTRACTABLE MICROCAPSULES OF ACTIVATED CARBON, SUPER ACTIVATED CARBON, AND OTHER ADSORPTIVE AND REACTIVE MATERIALS

STATEMENT OF GOVERNMENT INTEREST

The invention described herein may be manufactured and used by or for the U.S. Government for governmental purposes without the payment of any royalties thereon or therefor.

FIELD

The aspects of the disclosed embodiments relate to water extractable microcapsules of activated carbon or super activated carbon and other adsorptive, e.g. metal organic frame work (MOF) compositions and/or multifunctional materials, membranes embedded with activated carbon, super activated carbon, MOF compositions and/or multifunctional materials or other adsorptive material as well as methods to form the aforementioned microcapsules and membranes and extract the microcapsules' wall.

BACKGROUND

Some air permeable chemical protective clothing currently in use by some North Atlantic Treaty Organization (NATO) countries, may contain activated carbon (surface area of 600-800 $m^2/g$), that affords protection from chemical warfare agent (CWA) vapors, but not to CWA contaminated aerosols and liquids. Some selectively permeable membranes based chemical/biological (CB) protective clothing (e.g., the All-Purpose Personal Protective Ensemble (AP-PPE), the Joint Chemical Biological Coverall for Combat Vehicle Crewman (JC3), the Integrated Footwear System (IFS) sock) provides CB agent protection, however, it is expensive and care must be taken to prevent tears in clothing since there is no secondary protection mechanism such as afforded by activated carbon.

Microencapsulation is a process that involves enclosing an inner core material with an outer shell wall material, producing a microcapsule. Microcapsules have received the most attention in recent years for controlled release of drugs (as in drug delivery) and protection of specific functional materials (i.e. medicinal drugs, food additives, perfumes, textiles, and industrial chemicals) for long periods of time.

Activated carbon has been used as an adsorbent for organic compounds because of its high surface area, high adsorption capacity, microporous structure, and specific surface activity. Activated carbon and some MOF compositions can absorb a variety of toxic chemicals (e.g., hazardous industrial and warfare liquid and vapor chemicals). Similarly, multifunctional materials can react to a variety of toxic chemicals (e.g., hazardous industrial and warfare chemicals).

Processes that incorporate activated carbon, MOF compositions and/or multifunctional particles into a membrane structure without particle encapsulation can result in particle poisoning (i.e., rendering them non-active, non-multifunctional, or with little remaining toxic vapor adsorptive capacity or reactivity).

It would be desirable to provide a membrane structure with activated carbon, super activated carbon, MOF compositions, and/or multifunctional particles where the process avoids particle poisoning (i.e., rendering activated carbon particles non-active, multifunctional particles non-multifunctional, active/multifunctional MOF particles non-active/non-multifunctional or with little remaining toxic vapor adsorptive and/or multifunctional capacity).

It would be desirable to provide CB protective clothing for the Warfighter operating in a CB agent/toxic industrial chemical contaminated battlefield environment a fabric system that is lightweight, flexible, waterproof, moisture vapor permeable, launderable, and provide protection against warfare agents, toxic industrial chemicals, and deadly bacteria and viruses.

SUMMARY

In one embodiment, a microcapsule is provided. The microcapsule includes a particle core selected from activated carbon (AC), super activated carbon (SAC), metal organic framework (MOF) composition, multifunctional material or a mixture thereof and a water-soluble polymer shell.

In another embodiment, a method of forming microcapsule is provided. The microcapsule includes a particle core selected from activated carbon (AC), super activated carbon (SAC), MOF composition, multifunctional material or a mixture thereof; and a water-soluble polymer shell. The method includes mixing particle core material, water-soluble polymer and solvent to form a solution, atomizing the solution to form liquid droplets and drying the liquid droplets to substantially evaporate the solvent and harden the water-soluble polymer and form the water-soluble polymer shell around the particle core material.

In another embodiment, a method of applying activated carbon (AC), super activated carbon (SAC), MOF composition, multifunctional material or a mixture thereof to a membrane is provided. The method includes providing a microcapsule including (1) a particle core selected from activated carbon (AC), super activated carbon (SAC), MOF composition, multifunctional materials or a mixture thereof and (2) a water-soluble polymer shell, applying the microcapsule to the membrane including water-soluble microsized particles comprising particles comprising salt, sugar or polysaccharide and exposing the membrane and microcapsule applied thereto to water to dissolve the water-soluble polymer to embed the particle in the membrane.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 3 is a table showing the spray-drying formulations of Examples 1-16;

FIG. 5 is a table showing analysis data for Examples 1-16.

DETAILED DESCRIPTION

Microcapsules of activated carbon (AC), super activated carbon (SAC), multifunctional material, MOF composition, or a mixture thereof can be used to produce porous membranes (e.g., microporous and ultraporous, preferably, microporous) that are lightweight and flexible as well as a liquid, aerosol, and vapor proof barrier to both toxic chemicals, bacteria, and viruses, yet are permeable to moisture vapor for improved users' comfort while working in a contaminated environment. Useful applications include, for example, protecting soldiers from such hazards as well as protecting industrial chemical/fuel handlers, bio-hazard emergency responders and medical personnel and their use in CB protective tents/shelters, contaminated air filtration systems for hospitals and clean rooms, etc.

Aspects of the disclosed embodiments are directed to water extractable microcapsules of AC, SAC, multifunctional material, MOF composition, or a mixture thereof that are produced using a water-soluble polymer, such as, for example, polyvinyl alcohol (PVOH), a polar solvent (e.g., water), and mini-spray drying techniques. The microencapsulation process using a water-soluble polymer is used to prevent the microcapsules' surface area and the AC, SAC, MOF composition, multifunctional material or a mixture thereof contained therein from adsorbing and/or reacting to unwanted processing liquids (e.g., lubricant, plasticizer, etc.) during the process of making AC, SAC, MOF composition, multifunctional materials, or a mixture thereof loaded protective membranes. Once integrated or loaded into a membrane, the water-soluble polymer microcapsules' shells are removed by dissolving them in water thereby embedding or loading the AC, SAC, MOF composition, multifunctional material, or mixture thereof into the membrane itself with their original adsorptivity and/or reactivity intact (i.e., unaffected).

Figure 1:
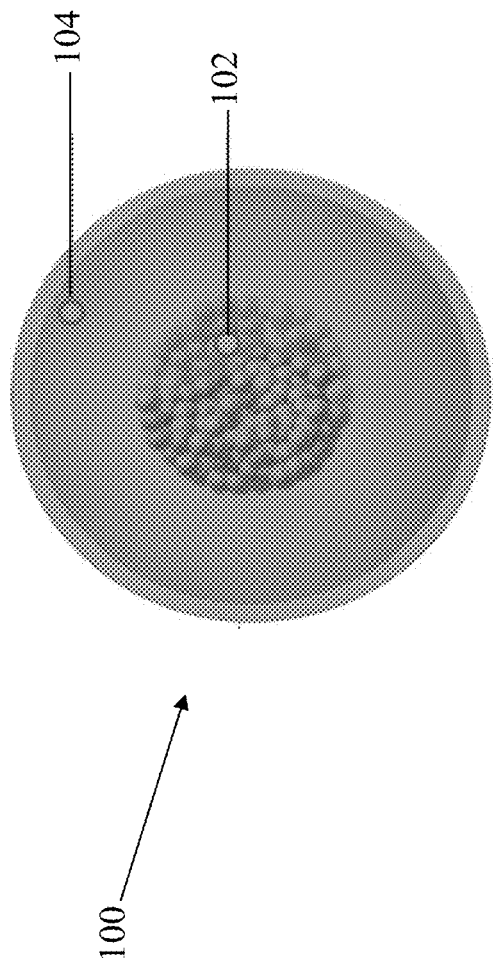
FIG. 1 is a schematic illustration of an embodiment of a microcapsule.

FIG. 1 is illustrative of aspects of one embodiment of a microcapsule of AC, SAC, MOF composition, multifunctional material, or a mixture thereof. Microcapsule 100 includes a water-soluble polymer shell 102, for example, PVOH, and a particle core of AC, SAC, MOF composition, multifunctional material, or a mixture thereof 104.

Carbon is activated under extreme heat to form AC, SAC or a mixture thereof, and emerges with sub-microscopic pores that can adsorb solvent molecules. The AC and SAC particle size distribution may range in size from about 500 microns to about 500 nanometers. The adsorptive capacity of AC, SAC or a mixture thereof is proportional to its surface area; therefore, it increases as its surface area increases. SAC can have an ultrahigh surface area of about 3,500 m$^2$/g. The AC, SAC or a mixture thereof adsorb chemical war agents (CWAs) and toxic industrial chemicals (TICs); therefore, it is used in protective clothing to protect soldiers and chemical handlers in CWA and TIC contaminated environments.

An MOF is composed of sulfur, cobalt, and carbon atoms. Similar to AC and SAC, MOF is a highly porous structure so it can adsorb and store gases like hydrogen and carbon dioxide. Its structure can also be extended/altered to contain catalytically reactive materials so that the catalytically reactive materials can then be incorporated into a membrane structure. As blended into a membrane structure, its uses include gas adsorption and energy storage via solar power conversion. MOF based CB protective materials can also be produced containing catalytically reactive functional groups for CB protective clothing applications.

Multifunctional materials are referred to many different materials that have different functions. For example, DEET and nepetalactone for insect repellence, metal oxides such as silver oxide or copper oxide, etc. as biocides, and halogens such as fluorine and bromine, etc. as flame retardants.

Water-soluble polymers include polyvinyl alcohol (PVOH), polyethylene glycol (PEG) and other water-soluble polymers such as, for example, PEG derivatives as well as micrometer-sized sugar (e.g., table sugar (or sucrose). A commercial source is Hosokawa Mikro ACM® (Air Classifying Mill) (ACM) having a size ranging from about 75 to less than about 20 microns, salts, polysaccharides (e.g., modified starch for textile industry from Angel Starch & Chemicals PVt., etc. preferably PVOH. (e.g., Nichigo's G-Polymer™).

Another embodiment includes a method of forming the extractable microcapsules of AC, SAC, MOF composition, multifunctional material or a mixture thereof. In general, aspects of the method may include preparing a liquid solution of the water-soluble polymer, solvent and AC, SAC, MOF composition, multifunctional material or a mixture thereof. The concentration of water-soluble polymer can range from about 0.33% to about 10%. The concentration of AC, SAC, MOF composition, multifunctional material or a mixture thereof can range from about 0.33% to about 10% (e.g., about 0.33 g to about 10 g in a 100 ml solution), and the AC, SAC, MOF and multifunctional material size may range in size from about submicron to preferably less than 500 microns. The solvent can be polar and can include water, alcohol (e.g., distilled water, and methanol), preferably water, one aspect of water being its use for an environmentally friendly extraction process. Preferably, the water-soluble polymer is dissolved in the solvent, e.g., water, before the AC, SAC, MOF composition, multifunctional material or a mixture thereof particle powder is added to the mixture. Once all these materials are added, stirred, and dissolved in a container, the formulation is ready for the spray drying process.

An embodiment can include a spray drying process performed in two stages. In the first stage (atomization), liquid solution (including the water-soluble polymer, solvent and AC, SAC, MOF composition, multifunctional material or a mixture thereof) can be fed by an air stream through an electric heater into the spray cylinder (or drying chamber). The liquid solution/air stream is broken down and turned into micrometer size liquid droplets after going through an atomizer (or a nozzle) located at the top of the spray chamber. In the second stage (cooling and separation), the liquid droplets continue to dry, cool down, and form into microcapsules of the water-soluble polymer and AC, SAC, MOF composition, multifunctional material or a mixture thereof as they are channeling through a cyclone chamber (powder collector). This is where the microcapsules are separated from the air stream and fall down into the product collection vessel. As the solvent (e.g., water) evaporates, the microcapsules' shell material, the water-soluble polymer, hardens around the core material, AC, SAC, MOF composition, multifunctional material or a mixture thereof.

Figure 2:
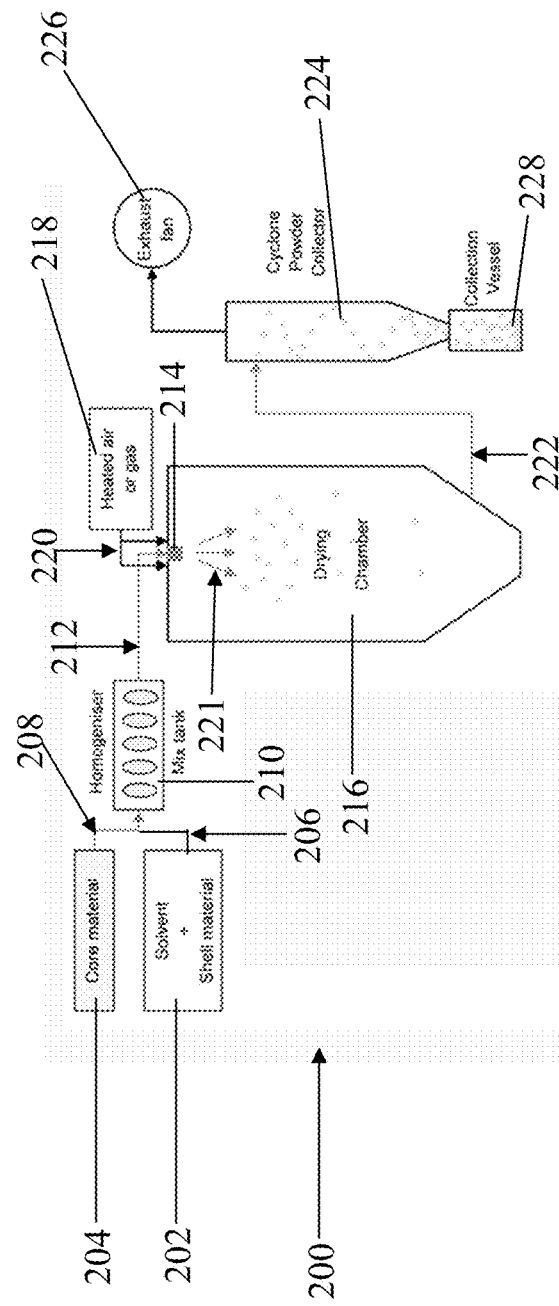
FIG. 2 is a schematic illustration of an embodiment of a mini spray dryer.

A mini spray dryer, such as, for example, a Buchi Mini Spray Dryer B290 can be used as is illustrated in FIG. 2. The mini spray dryer 200 exemplified in FIG. 2 includes solvent and polymer (water-soluble polymer shell material) 202 and core material (AC, SAC, MOF composition, multifunctional material or a mixture thereof) 204. The solvent and polymer 202 and core material 204 are conveyed by conduits 206 and 208, respectively, into a mixing tank 210. The mixing tank 210 may include an agitation apparatus, such as, for example, a homogenizer, to mix the solvent and polymer 202 and core material 204 and keep the mixture in a substantially uniform state. The substantially uniform mixture of solvent and polymer 202 and core material 204 may be then conveyed via conduit 212 and through nozzle 214 into drying chamber 216 where that mixture may encounter generated heated air or gas 218 that is conveyed through conduit system 220 into drying chamber 216 where liquid droplets 221 of the solvent and polymer 202 and core material 204 are formed. The liquid droplets 221 so formed may begin to dry through solvent evaporation and may be conveyed through conduit 222 into cyclone powder collector 224 for further solvent evaporation where exhaust fan 226 generates air agitation in the cyclone powder collector 224 where the microcapsules of core polymer and core material formed and are collected in collection vessel 228. The conditions set, for example, on the mini-spray dryer: (1) Inlet Temperature: 140° C.; (2) Pump Rate: 30%; (3) Aspirator Rate: 95%; and (4) Nozzle Cleaning: 3 times. These conditions were fixed for spray drying all formulations.

Embodiments also include the microcapsules incorporated into a porous membrane (e.g., microporous or ultraporous, preferably, microporous), for example, polyurethane, and the microcapsules' shell walls then removed to restore AC's. SAC's, MOF composition's, multifunctional material's or mixture thereof's adsorptive properties—resulting in a membrane that contains trapped AC, SAC, MOF composition, multifunctional material or mixture thereof particles. Other than polyurethane, the porous membrane material can be, for example, silicone, polyester or polyethylene. The porous membranes preferably include microsized salt particles or other water-soluble particles incorporated therein. The water extractable SAC, MOF composition, multifunctional material microcapsules that can be incorporated into a porous membrane, thus allow for water to reach and remove the water extractable microcapsule water-soluble polymer walls around SAC, MOF composition, multifunctional material particles embedded in the membrane during an extraction process allowing them to be active.

Aspects of such embodiments include a process for incorporating the microcapsules into a membrane, preferably a microporous membrane containing water-soluble particles including, for example, microsized particles of salts, sugar, polysaccharides, etc., and incorporating, embedding or loading the microencapsulated AC, SAC, MOF, multifunctional materials or mixture thereof into the membrane itself. Aspects of that process include exposing, coating or immersing the membrane with the microsized salt particles or other water-soluble particles incorporated therein to the microparticles encapsulated with AC, SAC, MOF composition, multifunctional material or mixture thereof. Next, the microparticle coated membrane can be submerged or exposed to water, using, for example a water bath, or a continuous water extraction assembly where fresh water is continuously flowing to dissolve and carry away the water-soluble polymer that made up the microcapsules and contained within the membrane structure. After the water treatment, the membrane is dried to remove water therefrom. The water-soluble particles incorporated into the membrane can create micropores (i.e., microporous structures) needed for water to come into contact with the microencapsulated AC, SAC, MOF, or other multifunctional particulates. These are done at specific volumetric flow rate (for spray drying process) temperature and time for both spray drying and extraction processes. The membrane can include ultraporous and microporous structure similar to that of an open pore sponge and with a hydrostatic resistance pressure of greater than 10 to 100 psi, and can be composed of, for example, polyurethane, silicone, polyester, polyethylene, fluorinated polymer and/or elastomers, etc.

Aspects of other embodiments include when the shell walls of microcapsules embedded within a membrane, preferably a porous membrane, are removed by dissolving in water in a water extraction process, the resulting membrane includes exposed AC, SAC, MOF composition, multifunctional material or mixture thereof particles. Another-embodiment may include the so formed membrane with exposed AC, SAC, MOF composition, multifunctional material or mixture thereof particles being laminated in between a shell fabric (e.g., 50% nylon and 50% cotton army combat uniform) and a comfort liner fabric (e.g., 1 oz./yd. 2 nylon tricot knit liner fabric) to form a fabric system. Aspects of the lamination process include transferring AC, SAC, MOF composition, or multifunctional material containing membrane into calendering rolls where the shell, liner, and 2 layers of web adhesives fabrics are also fed into the same calendering equipment to bond (or sandwich) the AC, SAC, MOF composition, or multifunctional material containing membrane in between the shell and liner fabric under certain processing conditions (temperature, pressure, and laminating speed). The resulting fabric system is lightweight, flexible, waterproof, moisture vapor permeable, launderable, and provides protection against warfare agents, toxic industrial chemicals, and deadly bacteria and viruses.

EXAMPLES 1-16

16 spray-drying formulations (see the table in FIG. 3) were created with different amounts of Activated Carbon, PVOH, and water using JMP 11 Design of Experiments (DoE) software. JMP is a statistical analyses and design of experiment (DOE) software, that was used to reduce the formulations needed for this research's experimental design, where the formulations were automatically varied to contain different amounts of activated carbon (AC), poly(vinyl alcohol) (PVOH), and deionized water (see FIG. 3)

First, each formulation was prepared by adding the weighed PVOH into the known volume of deionized water, under continuous stirring and heating to completely dissolve the PVOH. Second, the weighed AC was slowly added to the PVOH/water solution (giving a black colored slurry appearance) under constant stirring at room temperature for 30 minutes. Once all the materials were added, stirred, and dissolved in a container, the formulation was ready for the spray drying process.

The spray drying process next took place in two stages using a Buchi Mini Spray Dryer B290. Conditions set on the mini-spray dryer for all formulations included: (1) Inlet Temperature: 140° C.; (2) Pump Rate: 30%; (3) Aspirator Rate: 95%; and (4) Nozzle Cleaning: 3 times. In stage 1 (atomization): Each liquid solution (as represented in the above formulations) was fed by an air stream through an electric heater into the spray cylinder (or drying chamber). The liquid solution/air stream was broken down and turned into micrometer size liquid droplets after going through an atomizer (or a nozzle) located at the top of the spray chamber. In stage 2 (cooling and Separation): liquid droplets continued to dry, cool down, and form into PVOH/AC. This is where the microcapsules were separated from the air stream and fell down into the product collection vessel (as the solvent (water) evaporated, the microcapsules' shell material hardened around the core material).

Analyses of the resulting SAC microcapsule yielded the following:

(1) microcapsules' yields collected varied among all the formulations and, generally, formulations of lower yields (i.e. 9, 10, and 13) are attributed to the high signatures of webbing that occurred in the drying chamber, causing entryway blockage to the cyclone chamber and the collection vessel of the spray dryer.

(2) Microcapsule size varied in the approximate range of 1 mm to 50 mm in diameter. Uniformity on the basis of size and shape varied among the formulations, microcapsule shapes were found to be perfectly spherical, containing one or more indentations, and jagged. The degree of clustering varied among the formulations. For instance, in the set of formulations shown below, formulation 6 showed a high degree of clustering; formulations 1 and 13 showed an intermediate level of clustering; and formulations 2 and 9 showed the lowest degree of clustering with more dispersity among the microcapsules.

Figure 4:
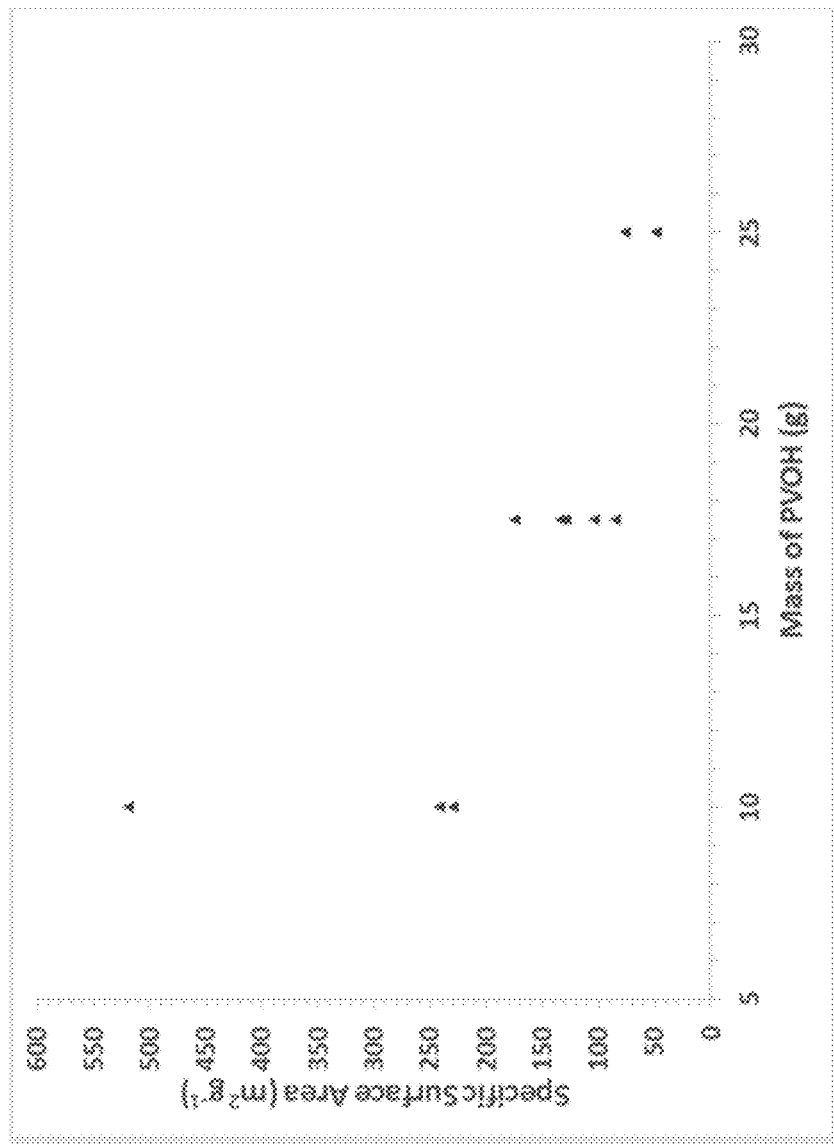
FIG. 4 is a graphical representation of data for Example, 1-16 of the specific Brunauer-Emmett-Teller (BET) surface area vs. mass of PVOH.

(3) Specific surface areas measured ranged from 48.36 $m^2/g$ (formulation 2) to 519.7 $m^2/g$ (formulation 12). In the plot shown in FIG. 4 that graphs the microcapsule's specific (BET) surface area versus the mass of PVOH (g), the trend was that the surface area decreased with respect to an increase in the mass of PVOH. It is reported that the surface area of activated carbon is about 3000 $m^2/g$ and this is in agreement to what was measured (run 1: 2398 $m^2/g$; run 2: 3574 $m^2/g$).

(4) Formulation 12 includes 25 grams of polymer, 250 milliliters of water, and 10 grams of Super Activated Carbon.

(5) More water and polymer in the formulation composition results in more collapses of the microcapsules.

(6) Increasing polymer (PVOH) content (to encapsulate the activated carbon) in the formulation composition results in larger microcapsule sizes.

(7) Lowering polymer (PVOH) content, results in smaller, and irregular shaped microcapsules.

In FIG. 5, data for Examples 1-16 include both microcapsule clustering and uniformity on the basis of size and shape were rated on a scale of 1 to 3, with 1 being the lowest level and 3 being the highest level.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A membrane comprising:
a microporous structure having a plurality of microcapsules embedded therein;
each microcapsule, consisting of:
   a. a particle core consisting of activated carbon (AC) and a multifunctional material consisting of at least one of an insect repellent, a biocide, and a halogen; and
   b. a shell consisting of a water-soluble polymer.

2. The membrane of claim 1, wherein the water-soluble polymer is polyvinyl alcohol (PVOH).

3. The membrane of claim 1, wherein the AC and the multifunctional material has a range in particle size of from about 500 nanometers to about 500 microns.

* * * * *